US006179821B1

(12) United States Patent
Caspary et al.

(10) Patent No.: US 6,179,821 B1
(45) Date of Patent: Jan. 30, 2001

(54) MEMBRANE PORT FOR A CONTAINER

(76) Inventors: Glenn A. Caspary, 18029 Hill Country Skyline, Austin, TX (US) 78736; Ralph E. Saunders, 200 County Rd. 133, Hutto, TX (US) 78634

(*) Notice: Under 35 U.S.C. 154(b), the term of this patent shall be extended for 0 days.

(21) Appl. No.: 09/099,282

(22) Filed: Jun. 18, 1998

(51) Int. Cl.[7] ..... A61B 19/00

(52) U.S. Cl. ..... 604/403; 604/415; 206/807; 215/324; 215/901

(58) Field of Search ..... 604/403, 405, 604/411, 262, 256, 905; 251/149.1, 149.7, 149.6; 215/250, 324, 901; 206/807; 137/614.18, 614.19

(56) References Cited

U.S. PATENT DOCUMENTS

| | | | | |
|---|---|---|---|---|
| 4,294,250 | * | 10/1981 | Dennehey | 128/247 |
| 4,607,671 | * | 8/1986 | Aalto et al. | 141/329 |
| 4,779,997 | * | 10/1988 | Schmidt | 383/96 |
| 5,108,702 | * | 4/1992 | Hubner | 604/415 |
| 5,334,180 | * | 8/1994 | Adolf et al. | 604/411 |
| 5,353,837 | * | 10/1994 | Faust | 137/614.18 |
| 5,501,426 | * | 3/1996 | Atkinson et al. | 251/149.1 |
| 5,628,726 | * | 5/1997 | Cotter | 604/4 |
| 5,728,087 | * | 3/1998 | Niedospial, Jr. | 604/408 |
| 5,755,712 | * | 5/1998 | Szempruch et al. | 604/403 |

FOREIGN PATENT DOCUMENTS

| | | |
|---|---|---|
| 2333944 | 7/1973 | (DE) . |
| 9728775 | 7/1997 | (DE) . |
| 2030956 | 8/1979 | (GB) . |

* cited by examiner

*Primary Examiner*—John G. Weiss
*Assistant Examiner*—David J. Cho
(74) *Attorney, Agent, or Firm*—Brian R. Woodworth

(57) ABSTRACT

A membrane port. The membrane port includes a flow port portion defining a lumen therethrough. A frangible connector portion is mounted on an enlarged portion of the flow port portion. A pierceable membrane is disposed in the lumen defined through the flow port portion to prevent fluid flow through said lumen. A cover portion is mounted on the frangible connector portion. The cover portion is constructed to fluidly seal a first end portion of the flow port portion.

6 Claims, 2 Drawing Sheets

MEMBRANE PORT FOR A CONTAINER

TECHNICAL FIELD

The present invention relates generally to an access port for an associated container, and more particularly to an access port having a pierceable membrane, and an outer cover portion that is frangibly removable therefrom, whereby the membrane of the access port remains sealed until the cover portion is removed and a piercing member is inserted through the membrane for fluid access to the contents of the container.

BACKGROUND OF THE INVENTION AND TECHNICAL PROBLEMS POSED BY THE PRIOR ART

Administration of intravenous solutions and the like for patient healthcare is typically effected through the use of solution containers having one or more access ports, some of which are sealed by pierceable membrane elements. Such pierceable membranes act to seal the contents of the container until access is required, with the membrane being pierceable through the use of a piercing member such as a spike of an associated tubing set or a hypodermic needle. The piercing member can be manipulated to penetrate the membrane, thereby fluidly connecting the hollow interior of the piercing member with the interior of the container. Flow of liquid through the access port, via the piercing member, is thus provided in a convenient and efficient fashion.

In order to avoid contamination of the solution within a container, the pierceable membrane of a container is typically provided with a suitable overcap or closure which covers the membrane and seals it against contamination prior to the juncture at which the contents of the container are to be used. Of course, the provision of such a protective closure adds to the manufacturing cost of the container. Additionally, the protective closure can be subject to inadvertent damage attendant to handling of the container, which can impair the sealing integrity of the closure and thus render the container unsuitable for use.

The present invention is directed to an improved access port element having a pierceable membrane, and an integral protective cover which facilitates efficient and economical use thereof, with the port element configured to maintain its sealing integrity attendant to normal handling and use of the container.

SUMMARY OF THE INVENTION

A membrane port embodying the principles of the present invention is configured for mounting on an associated container of known construction, such as a flexible bag for an intravenous solution. The membrane port includes an integral pierceable membrane element which can be penetrated by an associated piercing pin or like element for joining a tubing set or other fluid handling arrangement in fluid communication with the interior of the container. Notably, the membrane port is provided with an integral cover portion which is frangibly, removably joined to the port so that the seal integrity of the port is maintained prior to removal of the cover portion. The cover portion is configured for convenient manipulation and removal when access to the contents of the container is required.

In accordance with the illustrated embodiments, the present membrane port includes a port body having a generally tubular flow port portion, and a removable cover portion sealing one end of the flow port portion. The flow port portion includes a pierceable membrane which can be penetrated by an associated piercing member of known construction to allow fluid flow through the tubular port portion. Such a piercing member (sometimes referred to as a “spike”) is typically joined to an associated tubing set to provide access to the contents of a container to which the membrane port is fitted.

The cover portion of the membrane port is removably joined to the flow port by a frangible connector portion. By fracture of the connector portion, the cover portion can be separated from the flow port portion, thereby providing access to the pierceable membrane from the end of the flow port portion which is initially sealed by the cover portion. In a preferred embodiment, the cover portion includes at least one outwardly extending projection to facilitate grasping of the cover portion for its manipulation and removal by fracture of the connector portion.

In one embodiment of the present invention, the flow port portion includes an outwardly extending, preferably outwardly flared, load-absorbing region to which the frangible connector portion is joined. By this configuration, an annular space is defined between the flow port portion and the cover portion. The load-absorbing region is positioned intermediate the openable end of the flow port portion and the pierceable membrane. The provision of the load-absorbing region has been found to reduce premature failure of the connector portion while still permitting the connector portion to be fractured as required for removal of the cover portion.

In the preferred form, the tubular flow port portion includes an insertion section which extends outwardly from the load-absorbing region, with the insertion section thus being configured to receive a piercing member such as a spike associated with a tubing set. The insertion section desirably acts to guide the movement of the piercing member as it is inserted into the flow port portion to pierce the membrane of the port. The insertion section also desirably acts to isolate and separate the interior passage of the flow port portion from the frangible connector portion, helping to avoid “touch contamination” attendant to removal of the cover portion.

Other features and advantages of the present invention will become readily apparent from the following detailed description, the accompanying drawings, and the appended claims.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
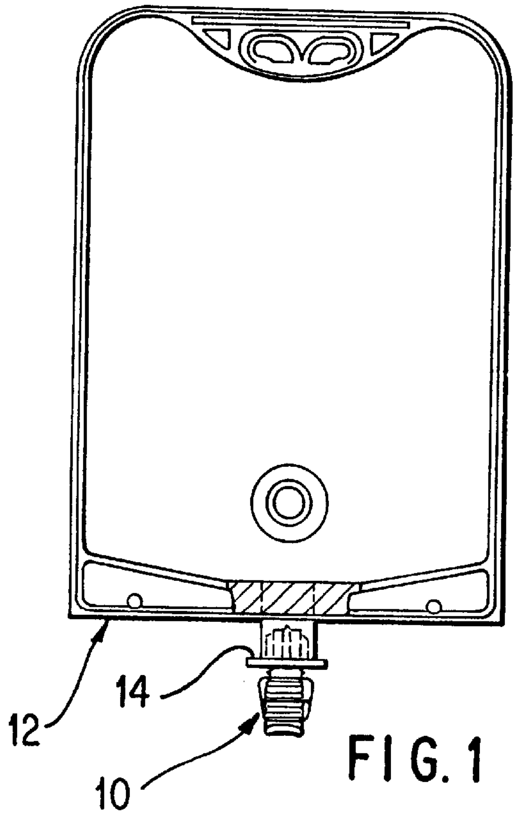
FIG. 1 is a side elevational view of a container having a membrane port embodying the principles of the present invention.

While the present invention is susceptible of embodiment in various forms, there is shown in the drawings and will hereinafter be described presently preferred embodiments of the present invention, with the understanding that the present disclosure is to be considered as an exemplification of the invention, and is not intended to limit the invention to the specific embodiment illustrated.

With reference to FIG. 1, a membrane port 10 embodying the principles of the present invention is shown for use in a typical application mounted on an associated fluid container 12. Container 12 is of a known type frequently employed for storage, handling, and/or administration of intravenous solutions or the like. Container 12 can have a variety of constructions, including, but not limited to, polymeric bottles, glass bottles, ampules, and tubes. In the embodiment of the invention depicted in the accompanying figures, container 12 is a flexible pouch constructed from one or more plies of flexible polymeric material, heat-sealed or otherwise bonded at peripheral portions thereof to define the interior volume of the container.

The container can include a flanged port mount 14 on which the membrane port 10 is fixedly mounted, such as by heat-sealing, adhesive securement, or by other suitable means. The port mount 14 is of a generally tubular configuration, and thus provides fluid communication between the membrane port 10 and the interior of the container 12.

The contents of the container 12 can be administered to a patient through a tubing set of known construction (not shown). The tubing set preferably includes a piercing member, e.g., a spike of known construction, which is used to provide fluid communication between the interior of container 12 and the tubing set. The piercing member preferably includes a sharpened, hollowed pin or spike element constructed to penetrate a membrane of the membrane port 10, as described in detail herein. The membrane port 10 has been particularly configured to facilitate insertion of such a piercing member into the membrane port while maintaining the seal integrity of the port against contamination prior to accessing the contents of container 12.

Figure 2:
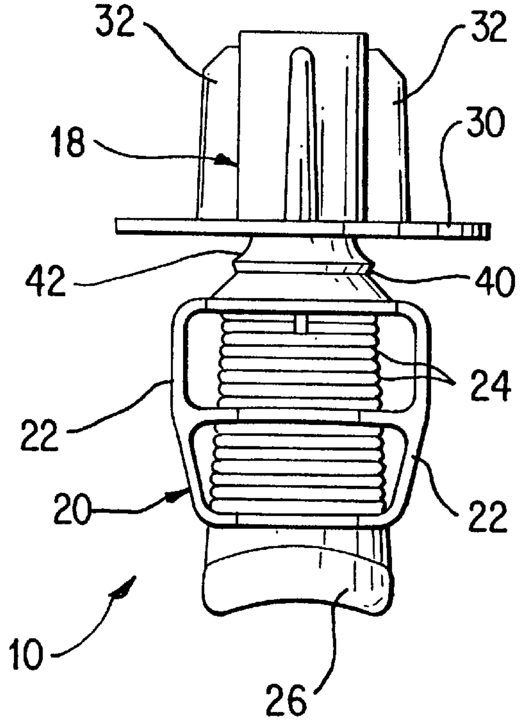
FIG. 2 is a side elevational view of the membrane port of the present invention.
Figure 3:
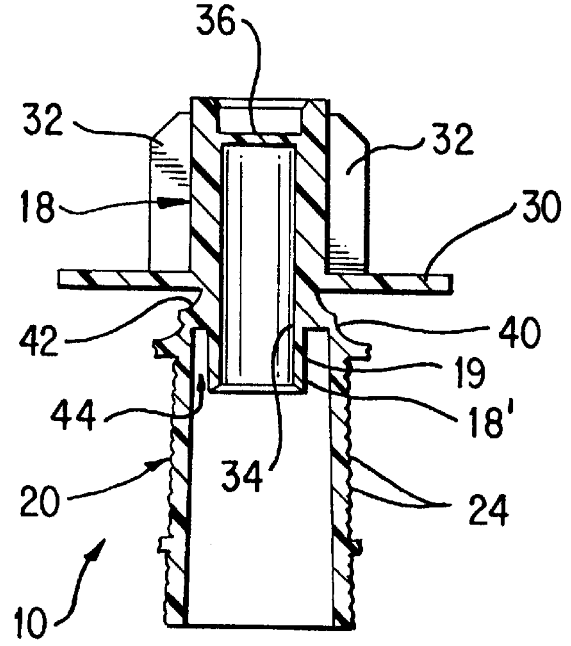
FIG. 3 is a cross-sectional view of the present membrane port, illustrated subsequent to molding and prior to sealing of a cover portion thereof.
Figure 4:
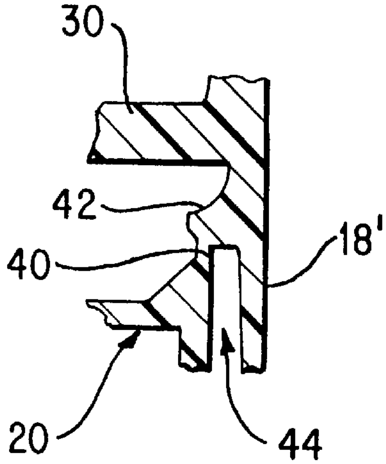
FIG. 4 is an enlarged, fragmentary cross-sectional view of the membrane port.

With particular reference to FIGS. 2 through 4, features of the membrane port 10 which facilitate use in this fashion will now be described. Membrane port 10 includes a generally tubular flow port portion 18 and a removable cover portion 20. The size and shape of membrane port 10, flow port portion 18, and cover portion 20 can be varied without departing from the scope of the invention defined by the appended claims. In the embodiment of the present invention depicted in the accompanying figures, membrane port 10 is substantially tubular in shape. Cover portion 20 is constructed to seal a first end portion 19 of flow port portion 18. The cover portion 20 closes and seals the membrane port, and protects it against contamination prior to removal of the cover portion.

Cover portion 20 can include at least one outwardly extending gripping projection 22 to facilitate removal of the cover portion 20. In the illustrated embodiment, two diametrically opposed gripping projections 22 are provided, and are configured so as to facilitate the application of finger pressure, in a twisting motion, to the cover portion, whereby the cover portion can be rotated relative to the flow port portion 18 for removal of the cover portion 20. is External ribs 24 also can be provided on the cover portion to further facilitate its convenient manipulation.

FIG. 3 illustrates a cross-sectional view of the membrane port 10, with this view oriented at 90° relative to the view of FIG. 2 (rotated about a longitudinal axis of the membrane port). FIG. 3 illustrates the membrane port subsequent to molding thereof, e.g., by injection molding, and it will be appreciated that the configuration of the membrane port facilitates efficient formation in this manner. Subsequent to molding, it is necessary to close and seal the construction, and thus by comparison of FIGS. 2 and 3 it will be observed that the end of cover portion 20 is sealed (such as by radio-frequency heat-sealing or other known methods) to form a sealed end 26. Thus, the sealed end 26 acts to close and seal flow port portion 18 against contamination and leakage prior to use.

In order to facilitate mounting of the membrane port on the port mount 14 of the container 12, the flow port portion 18 may include an annular mounting flange 30 which projects radially outwardly therefrom to provide a surface for securement to port mount 14 of container 12. One or more ribs 32 can be provided on the mounting flange (at 90° intervals in the illustrated embodiment) to provide greater structural rigidity to membrane port 10.

Fluid flow through the interior of the flow port portion 18 is provided by a lumen 34 defined by the flow port portion 18. In the depicted embodiment, lumen 34 extends substantially along the longitudinal axis of flow port portion 18. Sealing of the contents of the container 12 is provided by pierceable membrane 36 which extends across and seals lumen 34. The membrane 36 can be penetrated, such as by a piercing member of a tubing set as above-discussed, to allow fluid flow through the tubular flow port portion 18. Pierceable membrane 36 can be a separate element that is mounted using known techniques, e.g., heat sealing and adhesive bonding, within lumen 34. In the embodiment of the present invention depicted in the accompanying figures, pierceable membrane 36 is unitarily formed with the remainder of membrane port 10. It will be appreciated that the cost of membrane port 10 is reduced when it is of unitary construction, e.g., when membrane port 10 and pierceable membrane 36 are provided by a single injection molding.

By way of example, a current embodiment of the membrane port of the present invention is constructed of a polymeric material, e.g., polyvinylchloride (PVC), has an internal lumen diameter on the order of 0.215 inches, and a length, prior to formation of sealed end 26, of approximately 1.4 inches. In this embodiment, pierceable membrane 36 is provided with a substantially uniform thickness of about 0.02 inches. The materials from which membrane port 10 is formed can be varied, as will be understood by those skilled in the art. Further, the dimensions and the shape of membrane port 10 can be varied without departing from the spirit and scope of the present invention. It will be appreciated that membrane 36 is dimensioned to seal flow port portion 18, thereby containing the contents of container 12 within container 12. Membrane 36 also is preferably constructed such that it will maintain its seal integrity against normal pressures created within container 12 during handling of the container, while being sufficiently thin to permit its penetration, by a suitable piercing member, without application of undue force.

With further reference to FIGS. 2–4, membrane port 10 includes a frangible connector portion 40 which removably joins the cover portion 20 to the flow port portion 18 such that cover portion 20 seals membrane port 10 from an external environment thereof when cover portion 20 is fully connected to connector portion 40. As best illustrated in the fragmentary, cross-sectional view of FIG. 4, flow port portion 18 can include an enlarged, outwardly extending or outwardly flared, load-absorbing region 42. In the embodiment depicted in FIG. 4, cover portion 20 is connected by the connector portion 40 to a relatively thick portion of the load-absorbing region 42, thereby defining an annular space 44 between cover portion 20 and flow port portion 18. The provision of the load-absorbing region 42, and the manner in which the cover portion 20 is connected thereto by connector portion 40, have been found allow membrane port 10 to withstand loads exerted on cover portion 20 comparable to loads that occur during normal handling of container 12 without premature fracture of the connector portion 40. At the same time, this configuration facilitates convenient removal of the cover portion by application of torque thereto by twisting manipulation of the cover portion. It is believed that the relatively enlarged load-absorbing region 42 acts somewhat in the nature of a bellows-type spring to absorb loads exerted thereon by the cover portion 20 to protect the frangible connector portion against strain, while still permitting convenient manipulation of the cover portion 20, by a twisting motion, for its removal. Removal of the cover portion 20 exposes the lumen 34 and pierceable membrane 36 of flow port portion 18, and also permits insertion of a piercing member into flow port portion 18 for the piercing of pierceable membrane 36 and, thus, fluid communication with the interior of container 12.

In the above-described embodiment of the present membrane port, the connector portion 40 has a thickness of approximately 0.009 inches.

In accordance with the illustrated embodiment, the load-absorbing region 42 of the flow port portion 18 is positioned intermediate the pierceable membrane 36 and first end portion 19 of the flow port portion 18, i.e., the end that is covered and sealed by the cover portion 20. As above-discussed, first end portion 19 of flow port portion 18 preferably extends from the load-absorbing region 42 to define an insertion section 18', which is constructed to receive a piercing member and to guide the movement of the piercing member as it is advanced into lumen 34 defined by the flow port portion 18. Insertion section 18' also is constructed such that the piercing member can then be brought into engagement with and thereafter pierce membrane 36. Insertion section 18' acts to isolate the lumen 34 from the frangible connector portion 40, thereby avoiding "touch contamination" during "spiking", i.e., insertion of the piercing member into the interior of container 12.

Figure 5:
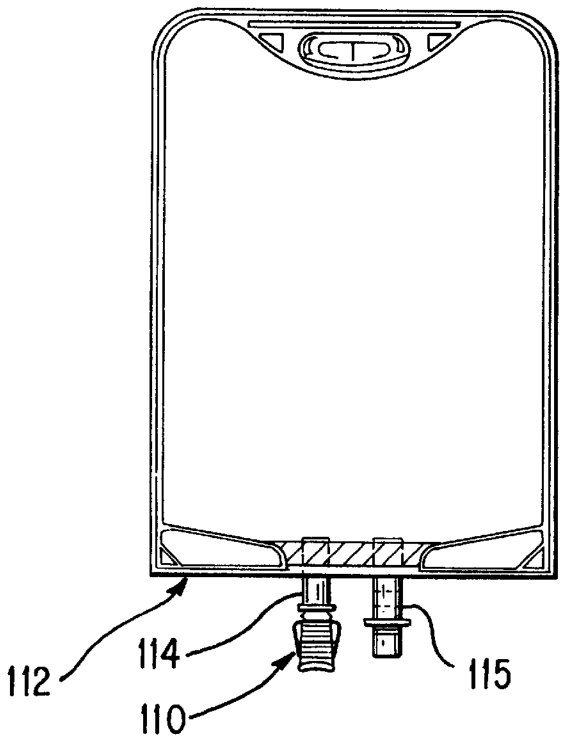
FIG. 5 is a side elevational view of a container having a membrane port configured in accordance with an alternate embodiment of the present invention.
Figure 6:
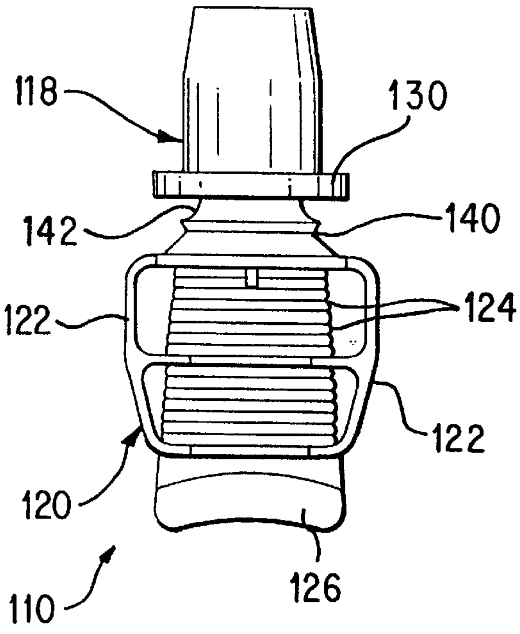
FIG. 6 is a side elevational view of the alternate embodiment of the present membrane port.
Figure 7:
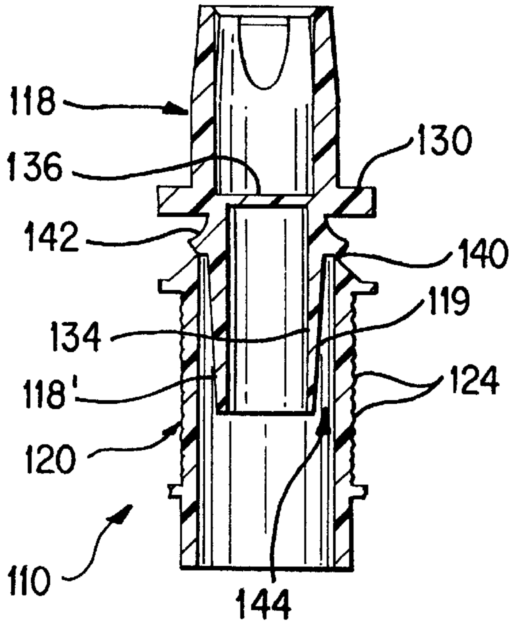
FIG. 7 is a cross-sectional view of the alternate embodiment of the present membrane port, subsequent to molding and prior to sealing of a cover portion thereof.

An alternate embodiment of the present invention is illustrated in FIGS. 5–7, with this alternate embodiment designated 110. Elements of this embodiment of the present invention, and associated components, like those described in the previous embodiment, are so-designated by like reference numerals in the one-hundred series.

Membrane port 110 is illustrated in position on an associated container 112 having a port mount 114 on which the membrane port 110 can be mounted. The container 112 is illustrated as including an auxiliary access port 115 positioned generally adjacent to the membrane port 110.

As particularly illustrated in FIGS. 6 and 7, the membrane port 110 includes a tubular flow port portion 118 and a cover portion 120 removably joined to the flow port portion. The cover portion 120 preferably includes at least one outwardly extending gripping projection 112 which facilitates grasping of the cover portion 120 for its removal. One or more exterior ribs 124 also can be provided to facilitate grasping of the cover portion. As in the previously discussed embodiment, it will be observed that the cross-sectional view of FIG. 7 illustrates membrane port 110 subsequent to molding, with the end of the cover portion open, while FIG. 6 illustrates the cover portion 120 after formation of sealed end 126, such as by radio-frequency heat-sealing or the like.

The flow port portion 118 includes a radially outwardly extending annular mounting flange 130 to facilitate mounting on the port mount 114 of container 112. Flow through the flow port portion 118 is via its internal lumen 134. Pierceable membrane 136 extends across the lumen 134 to seal the contents of the container 112 prior to penetration of the membrane 136 by a suitable piercing member.

As in the previous embodiment, the removable cover portion 120 is removably joined to the flow port portion 118 by a frangible, annular connector portion 140. The connector portion 140, in turn, is joined to an outwardly projecting, preferably outwardly flared, load-absorbing region 142 of flow port portion 118. By this arrangement, an annular space 144 is defined between the cover portion 120 and first end portion 119 of the flow port portion 118. The load-absorbing region 142 is preferably positioned intermediate the membrane 136 and first end portion 119 of the flow port portion 118 covered by the cover portion 120. The flow port portion 118 preferably extends from the load-absorbing region 142 to define an insertion section, 118', which receives the membrane-penetrating element of an associated tubing set or the like.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure and the appended claims are intended to cover all such modifications as fall within the scope of the appended claims.

What is claimed is:

1. A membrane port comprising:

a flow port portion having a first end portion and a second end portion, said flow port portion defining a lumen therethrough from said first end portion to said second end portion, said second end portion constructed to engage a fluid container;

a frangible connector portion having a first end portion and a second end portion, said second end portion of said connector portion mounted on said flow port portion;

a pierceable membrane disposed in said lumen defined through said flow port portion, said pierceable membrane constructed to prevent fluid flow through said lumen defined through said flow port portion; and a cover portion mounted on said first end portion of said connector portion, said cover portion constructed to seal said first end portion of said flow port portion from an external environment of said flow port portion, whereby said cover portion can be removed from said membrane port by breaking said frangible connector portion, thereby providing access to said lumen defined through said flow port portion and to said pierceable membrane.

2. A membrane port in accordance with claim 1, wherein said flow port portion includes an outwardly flared region, and wherein said second end portion of said connector portion is mounted on said outwardly flared region of said flow port portion.

3. A membrane port in accordance with claim 2, wherein an annular space is defined between said flow port portion and said cover portion.

4. A membrane port in accordance with claim 1, wherein said flow port portion has a first external diameter along its first end portion, said flow port portion having an enlarged region having a second external diameter larger than said first diameter, said enlarged region disposed between said first end portion and said second end portion of said flow port portion, and wherein said second end portion of said connector portion is mounted on said enlarged region of said flow port portion.

5. A membrane port in accordance with claim 4, wherein an annular space is defined between said flow port portion and said cover portion.

6. A fluid container comprising:

a container defining an interior space and constructed to fluidly retain a fluid in said interior space; and a membrane port mounted on said container, said membrane port comprising:

a flow port portion having a first end portion and a second end portion, said flow port portion defining a lumen therethrough from said first end portion to said second end portion, said second end portion engaging said container, said lumen in fluid communication with said interior space defined by said container;

a frangible connector portion having a first end portion and a second end portion, said second end portion of said connector portion mounted on said flow port portion;

a pierceable membrane disposed in said lumen defined through said flow port portion, said pierceable membrane constructed to prevent fluid flow through said lumen defined through said flow port portion, whereby said pierceable membrane fluidly seals said interior space defined by said container from an external environment of said container; and a cover portion mounted on said first end portion of said connector portion, said cover portion constructed to seal said first end portion of said flow port portion from an external environment of said flow port portion, whereby said cover portion can be removed from said membrane port by breaking said frangible connector portion, thereby providing access to said lumen defined through said flow port portion and to said pierceable membrane.

* * * * *